(12) United States Patent
Sobe (10) Patent No.: US 7,197,354 B2
(45) Date of Patent: Mar. 27, 2007

(54) SYSTEM FOR DETERMINING THE POSITION AND ORIENTATION OF A CATHETER

(75) Inventor: Lior Sobe, Raanana (IL)

(73) Assignee: Mediguide Ltd., Haifa (IL)

( * ) Notice: Subject to any disclaimer, the term of this patent is extended or adjusted under 35 U.S.C. 154(b) by 358 days.

(21) Appl. No.: 10/873,409

(22) Filed: Jun. 21, 2004

(65) Prior Publication Data

US 2005/0283067 A1 Dec. 22, 2005

(51) Int. Cl.
*A61B 5/00* (2006.01)
(52) U.S. Cl. .......................... 600/424; 600/407; 606/1
(58) Field of Classification Search ................ 600/407, 600/424; 606/1; 128/899; 324/207.11, 324/207.13, 207.23
See application file for complete search history.

(56) References Cited

U.S. PATENT DOCUMENTS

| 5,728,062 A | 3/1998 | Brisken |
| 5,850,682 A | 12/1998 | Ushiro .................. 29/608 |
| 6,353,379 B1 | 3/2002 | Busletta et al. ............. 336/200 |
| 6,711,429 B1 | 3/2004 | Gilboa et al. |

| 2002/0009535 A1 | 1/2002 | Michal et al. |
| 2003/0199852 A1 | 10/2003 | Seward et al. |

FOREIGN PATENT DOCUMENTS

JP 2002-372520 12/2002

OTHER PUBLICATIONS

International Search Report for parent PCT Application No. PCT/IL05/00586, Apr. 4, 2006 (4 pages).

*Primary Examiner*—Ruth S. Smith
(74) *Attorney, Agent, or Firm*—Edwards Angell Palmer & Dodge LLP (57) ABSTRACT

Electromagnetic field detector located within a catheter, for determining the position and orientation of the catheter according to an electromagnetic field generated in the vicinity of the catheter, the electromagnetic field detector including a ferromagnetic core having a perforation and at least one winding wound around the ferrous core, the perforation providing communication between a first side of the ferrous core and a second side of the ferrous core, the first side facing a proximal side of the catheter and the second side facing a distal side of the catheter, the winding producing a current according to the electromagnetic field, wherein the ferrous core increases the sensitivity of the electromagnetic field detector to the electromagnetic field, by increasing a proportionality factor between the current and the electromagnetic field.

20 Claims, 6 Drawing Sheets

SYSTEM FOR DETERMINING THE POSITION AND ORIENTATION OF A CATHETER

FIELD OF THE DISCLOSED TECHNIQUE

The disclosed technique relates to medical devices in general, and to methods and systems for determining the position and orientation of a catheter, in particular.

BACKGROUND OF THE DISCLOSED TECHNIQUE

While performing an operation on an artery or a vein, such as angioplasty or implanting a stent within an artery, it is necessary for the surgeon to know the position and orientation of the tip of the catheter during the operation. The position and orientation can be determined in different ways, for example, by means of an electromagnetic sensor, ultrasonic sensor, or a marker attached to the catheter.

U.S. Pat. No. 6,353,379 issued to Busletta et al., and entitled "Magnetic Device Employing a Winding Structure Spanning Multiple Boards and Method of Manufacturing thereof", is directed to a magnetic device which includes a magnetic core, a main circuit board, an overlay board and a plurality of conductors. The magnetic core includes a first portion and a second portion. The main circuit board and the overlay board include a winding structure. The main circuit board and the overlay include a first plurality of winding layers and a second plurality of winding layers, respectively. The conductors include a conductive via, a conductive post and a connector.

The overlay board is oriented parallel and proximate to the main circuit board. The first portion of the magnetic core is coupled to the main circuit board and the second portion of the magnetic core is coupled to the overlay board. The magnetic core is surface mounted to the main circuit board and to the overlay board. The conductive via are located on each of the main circuit board and the overlay board. The conductive post is located on the main circuit board and connects to the overlay board. The connector is coupled to an edge of the overlay board from the main circuit board. The conductors couple the first plurality of winding layers and the second plurality of winding layers together.

U.S. Pat. No. 5,850,682 issued to Ushiro and entitled "Method of Manufacturing Chip Type Common Mode Choke Coil", is directed to a chip type common mode choke coil which includes a plurality of non-magnetic sheets, a first plurality of magnetic sheets and a second plurality of magnetic sheets. On each of the non-magnetic sheets a conductor line at a predetermined orientation is printed. The non-magnetic sheets are stacked on the top of one another and the ends of the conductor lines are alternately connected by through holes. In this manner, part of the conductor lines form a figure-eight-shaped primary coil and the rest of the conductor lines form a figure-eight-shaped secondary coil.

A laminate is formed by placing the non-magnetic sheets between the first magnetic sheets and the second magnetic sheets and joining them together under pressure. A first hole (i.e., a core arranging hole) is formed at the center of the figure-eight-shaped primary coil and a second hole is formed at another center of the figure-eight-shaped secondary coil. Each of the first hole and the second hole is filled with a magnetic paste.

SUMMARY OF THE DISCLOSED TECHNIQUE

It is an object of the disclosed technique to provide a novel method and system for increasing the sensitivity of an electromagnetic field detector to an electromagnetic field.

In accordance with the disclosed technique, there is thus provided an electromagnetic field detector located within a catheter, for determining the position and orientation of the catheter according to an electromagnetic field generated in the vicinity of the catheter. The electromagnetic field detector includes a ferromagnetic core having a perforation and at least one winding wound around the ferrous core. The perforation provides communication between a first side of the ferrous core and a second side of the ferrous core. The first side faces a proximal side of the catheter and the second side faces a distal side of the catheter. The winding produces a current according to the electromagnetic field, wherein the ferrous core increases the sensitivity of the electromagnetic field detector to the electromagnetic field, by increasing a proportionality factor between the current and the electromagnetic field.

BRIEF DESCRIPTION OF THE DRAWINGS

The disclosed technique will be understood and appreciated more fully from the following detailed description taken in conjunction with the drawings in which.

DETAILED DESCRIPTION OF THE EMBODIMENTS

The disclosed technique overcomes the disadvantages of the prior art by providing an electromagnetic field detector, which includes a perforated ferromagnetic core within the coil of the electromagnetic field detector. The perforation in the coil, allows the passage of materials and elements which normally pass through the catheter, also to pass freely through the core. Alternatively, the perforation is employed to attach the electromagnetic field detector to another device which is incorporated within the catheter, such as an image detector. Further alternatively, the core includes a protrusion to fit a cavity in the device, in order to attach the electromagnetic field detector to the device in alignment with the longitudinal axis of the catheter.

Figure 1:
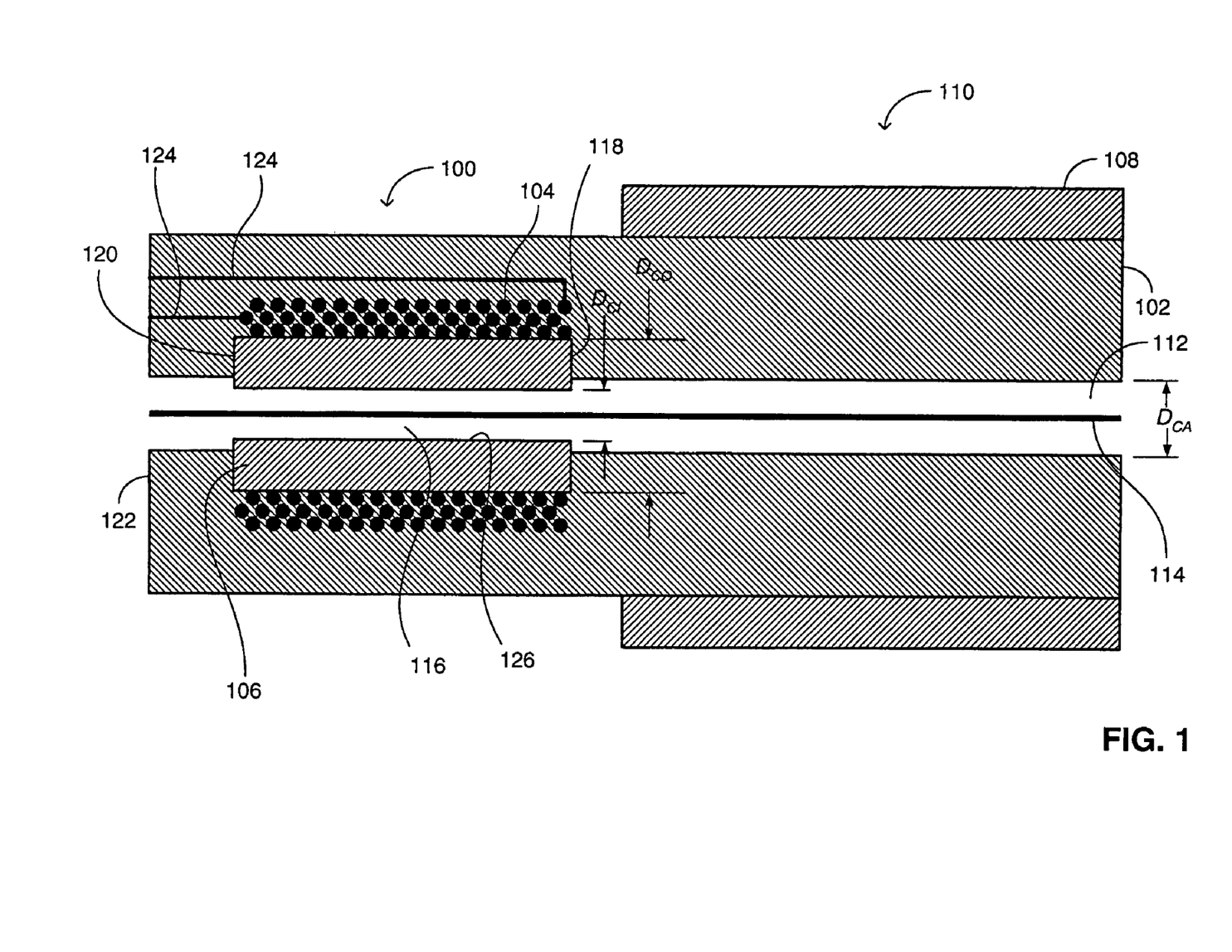
FIG. 1 is a schematic illustration of a cross section of an electromagnetic field detector, constructed and operative in accordance with an embodiment of the disclosed technique, and located within a catheter.

Reference is now made to FIG. 1, which is a schematic illustration of a cross section of an electromagnetic field detector, generally referenced 100, constructed and operative in accordance with an embodiment of the disclosed technique, and located within a catheter generally referenced 102. Electromagnetic field detector 100 includes an electromagnetic coil 104 and a core 106. Catheter 102 includes a medical operational element 108 at a distal portion 110 of catheter 102, a mid-portion (not shown) or a proximal portion (not shown) of the catheter. Electromagnetic field detector 100 is located substantially close to or at distal portion 110. Catheter 102 includes a longitudinal channel 112 for example for passage of a material or an element 114 there through. Material or element 114 can be for example, a guidewire for catheter 102, a liquid medication, and other elements or materials related to the operation of medical operational element 108, as further described herein below. The diameter of longitudinal channel 112 is referenced $D_{CA}$.

Core 106 includes a perforation 116 of a diameter designated by reference $D_{CI}$. Perforation 116 provides communication between a side 118 of core 106 and another side 120 of core 106. Side 118 points toward distal portion 110 and side 118 points toward a proximal portion 122 of catheter 102. The outer diameter of core 106 is referenced $D_{CO}$. Electromagnetic coil 104 is in form of a winding around core 106. Electromagnetic coil 104 is made of a wire having a substantially round cross section, or any other arrangement, such as rectangle, square, another polygon, and the like.

Electromagnetic coil 104 is coupled with a position and orientation determining system (not shown) by an electric conductor 124, for determining the position and orientation of catheter 102 or selected portions thereof, such as distal portion 110, or medical operational element 108. Alternatively, electromagnetic coil 104 is coupled with the position and orientation determining system via a wireless link. The position and orientation determining system can be similar to a medical positioning system (MPS) disclosed in U.S. Pat. No. 6,233,476 B1 which is assigned to the same assignee as that of the present patent application. Electromagnetic field detector 100 is embedded within catheter 102. The diameter $D_{CO}$ can be either substantially equal to, greater or smaller than diameter $D_{CA}$. The diameter $D_{CI}$ can be either substantially equal to, greater or smaller than diameter $D_{CA}$. The longitudinal axes of perforation 116 and longitudinal channel 112 are either substantially parallel or along the same line.

Core 106 is made of a material whose magnetic permeability is sufficient to impart a greater reactance to a bobbin or coil 104. This is particularly effective in case of relatively small coils Alternatively, core 106 can be made of a material whose permeability is negligible, such as polymer, glass, silicon, quartz, and the like. An abundance of materials inherent with high permeability is available. For this purpose, a ferromagnetic material is selected for core 106, such as iron, magnetite, Mu metal, Supermalloy, 4–79 Permalloy, and the like. Following is an explanation for the fact that the current generated by a magnetic circuit which includes a winding around a ferromagnetic core, in the presence of an electromagnetic field, is greater than a magnetic circuit which includes a winding (i.e., a coil, bobbin), without a ferromagnetic core.

Magnetic flux density B and magnetic field intensity H of a material in which a magnetic field exists, are related by $$B=\mu H \quad (1)$$

where $\mu$ is the permeability of the material. In a magnetic circuit whose inductance is L, having a core whose cross sectional area is A, and having a coil of N turns of winding, the electric current i generated by the electromagnetic field is $$i=NBA/L \quad (2)$$

Since the value of $\mu$ for a ferromagnetic material is larger than that of air by a few orders of magnitude, according to Equation 1, the magnetic flux density B in the magnetic circuit which includes electromagnetic coil 104 and core 106, is much greater than if the core was not present. Thus, according to Equation 2, the value of the electric current i generated in electromagnetic coil 104 in the presence of the electromagnetic field, is much greater than if no core was present, and therefore electromagnetic field detector 100 is substantially more sensitive to a given electromagnetic field, than an electromagnetic field detector without a core. In this sense, permeability $\mu$ can be regarded as a proportionality factor, by which the sensitivity of electromagnetic field detector 100 to the electromagnetic field is increased.

Medical operational element 108 can include a lumen intervention element, a lumen diagnostic element, a lumen imaging element, and the like. Medical operational element 108 is an element for performing medical operations in the lumen, such as modifying the characteristics of the lumen, or diagnosing the lumen, such as obtaining an image of the lumen. The characteristics of the lumen can be modified by performing a medical procedure thereon, such as percutaneous transluminal coronary angioplasty (PTCA), percutaneous transluminal angioplasty (PTA), vascularizing the lumen, severing a portion of the lumen or a plaque there within (e.g., atherectomy), providing a suture to the lumen, increasing the inner diameter of the lumen (e.g., by a balloon, a self expanding stent, a stent made of a shape memory alloy (SMA), or a balloon expanding stent) and maintaining the increased diameter by implanting a stent.

Medical operational element 108 can be further used to deliver substances to the lumen. For example, medical operational element 108 can be used to deliver a pharmaceutical substance to a selected site within the lumen, such as for inhibiting angiogenesis of cancerous cells, inhibiting metastasis, stimulating local hormonal activity of tissue cells and stimulating healing following a trauma. Medical operational element 108 can be further used for killing selected cells (either cancerous or non-cancerous) at the activation site of medical operational element 108 or in the vicinity thereof, by irradiating the cells with a radioactive substance, electric current, laser, or subjecting the cells to a cryogenic fluid, and the like. In this case, perforation 116 allows the radioactive substance, pharmaceutical substance or the cryogenic fluid to flow there through. For this purpose, an inner wall 126 of perforation 116 is coated with a biocompatible substance, such as Parylene, polyimide, Teflon, drug, a combination thereof, and the like, in order to avoid or prevent immune reactions in the body of the patient (not shown). The biocompatible substance can have either hydrophobic or hydrophilic properties. Alternatively, perforation 116 allows the electric conductor or the optical conductor (not shown) of medical operational element 108 to pass through.

Medical operational element 108 can further include, or be used for deployment of, a device within the lumen. Such a device can be for example, a valve (e.g., mitral valve, sphincter), suturing device, implant, biological marker, radiopaque marker, substance delivery device, imaging device, diagnostic device, miniature camera, infrared camera, optical coherence tomography (OCT), magnetic resonance imaging (MRI), intravascular ultrasound (IVUS), sensor, such as pressure sensor, temperature sensor, pH sensor, and the like. The sensor can be in form of a passive ultrasonic transducer, which transmits signals bearing the value of the detected parameter (pressure, temperature, pH etc.), in response to an ultrasonic wave directed from an external source toward the sensor. In this case, perforation 116 allows the electric or optical conductor (not shown) or medical elements of medical operational element 108, such as optical lens, and the like, to pass through. Perforation 116 allows the passage of a flexible shaft (not shown) which is employed for moving the imaging device, such as an IVUS.

Medical operational element 108 can also be used to perform a valvuloplasty operation (i.e., repair of an organic or an artificial valve). The lumen can be a portion of the vascular system, ureter, urethra, brain vessels, coronary vessels, vas deferens, lumens of the liver, kidney, lung (e.g., trachea and bronchus), digestive system, gal bladder, prostate gland, urogenital system, and the like. The lumen can be in the body of a human being as well as an animal.

Medical operational element 108 can be an expansion unit such as a balloon, stent, balloon expanding stent, an ablation unit such as laser, cryogenic fluid unit, electric impulse unit, cutting balloon, rotational atherectomy unit (i.e., rotablator), directional atherectomy unit, transluminal extraction unit, a substance delivery unit such as coated stent, drug delivery balloon, brachytherapy unit, and the like. In this case, perforation 116 allows medical elements, such as the balloon (not shown) in a deflated form, and the pressurized fluid conveying tube (i.e., a substance delivery lumen) thereof (not shown), to pass through.

The balloon expanding stent unit includes a stent which is located around a balloon. When the balloon is inflated, the stent expands. The cutting balloon unit includes a balloon having a plurality of blades on the periphery thereof, along the longitudinal axis of the catheter. The cryogenic fluid unit includes a fluid delivery lumen through which a fluid at a substantially low temperature is delivered to a desired site of the lumen. The electric impulse unit includes two electrical conductors. An electrical arc generated at the tip of the electrical conductors ablates the desired site of the lumen.

The rotablator includes a diamond coated tip which is coupled with an external motor via a flexible shaft. The flexible shaft rotates the diamond coated tip at a substantially high speed, wherein the diamond coated tip grinds calcified plaque which is formed on the inner wall of the lumen. The ground material enters the circulation.

The directional atherectomy unit includes a cutter and a balloon. The cutter is coupled with an external motor via a flexible shaft. The balloon pushes the cutter toward the sidewall opposite to the balloon, thereby allowing the cutter to cut the calcified plaque. The calcified particles are pumped out through the catheter. The transluminal extraction unit includes a cutter which is coupled with an external motor via a flexible shaft. The motor rotates the cutter, wherein the cutter cuts the calcified plaque and the calcified particles are pumped out through the catheter. In above cases, perforation 116 allows the flexible shaft (not shown) to pass through.

The coated stent is coated with a pharmaceutical substance, wherein the substance is released into a desired region of the lumen, when the coated stent is installed in the lumen. The drug delivery balloon is a balloon which is coupled to a source of a pharmaceutical substance, via a drug (i.e., substance) delivery lumen. The pharmaceutical substance exits the balloon through a plurality of micropores. In this case, perforation 116 allows the drug delivery balloon (not shown), substance delivery lumen (not shown), or both, to pass through. The brachytherapy unit includes a substance delivery lumen, through which radioactive palettes are delivered to a desired site within the lumen. The radioactive palettes remain at the desired site for a prescribed time and then are scavenged out through the substance delivery lumen. Thus, a prescribed dose of radiation is delivered to the desired site of the lumen. In this case, perforation 116 allows the substance delivery lumen (not shown) to pass through. It is noted that perforation 116 allows the passage of all elements and materials there through, which pass through longitudinal channel 112.

Electromagnetic coil 104 can be incorporated with an electric shield (not shown) in order to reduce interference due to an electric field. The electric shield encompasses the electromagnetic coil either entirely or partially. The electric shield can be for example in form of a complete cylinder or a partial cylinder whose cross section is in form of a partial circle. If the electric shield is in form of a partial cylinder, eddy currents are reduced.

The electric shield can be in form of an electrically conductive foil, an electrically insulating material (e.g., polymer) which is coated with an electric conductor, an electrically conductive paint, and the like. The electric shield is grounded. The electric conductor can be made of gold, copper, and the like.

Figure 2:
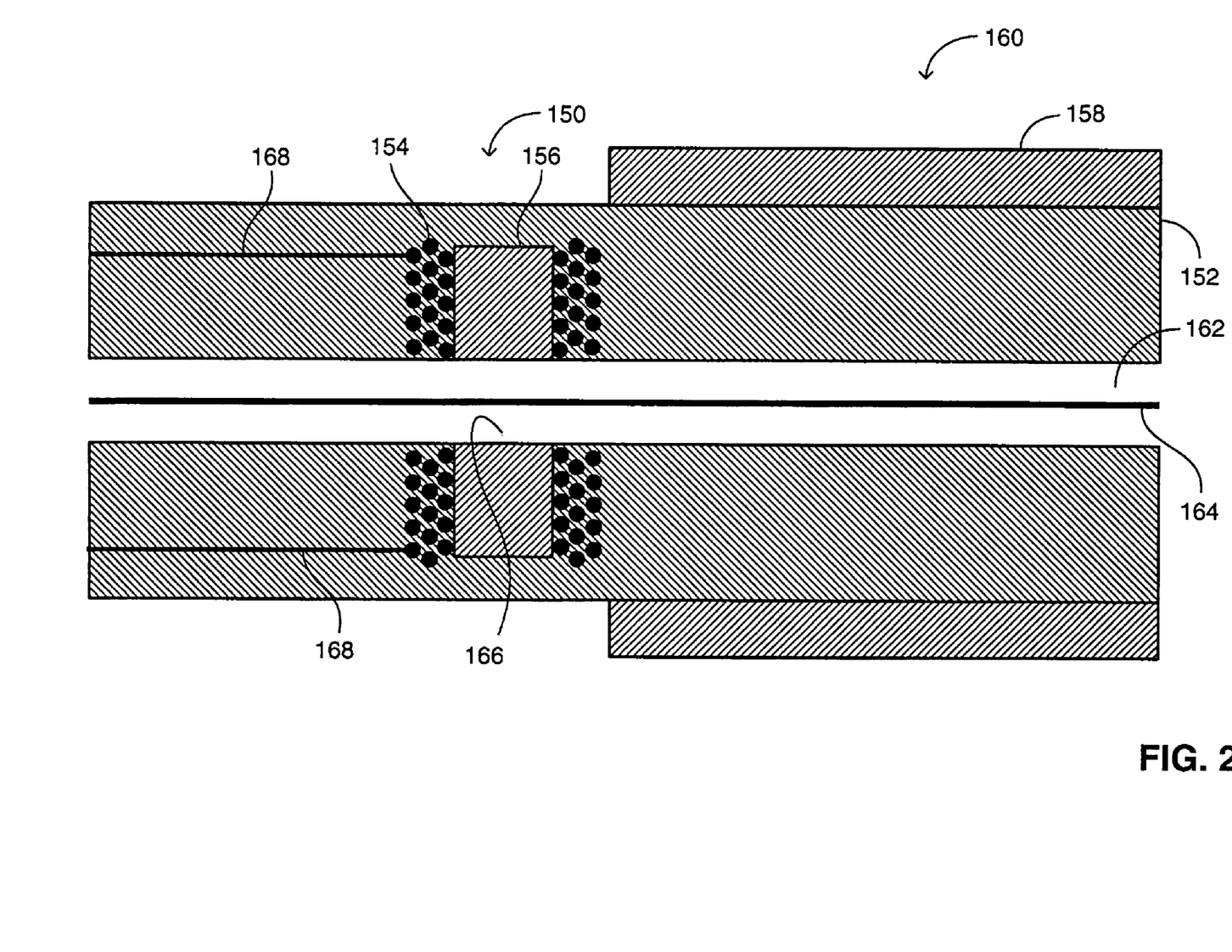
FIG. 2 is a schematic illustration of a cross section of an electromagnetic field detector, constructed and operative in accordance with another embodiment of the disclosed technique, and located within a catheter.

Reference is now made to FIG. 2, which is a schematic illustration of a cross section of an electromagnetic field detector, generally referenced 150, constructed and operative in accordance with another embodiment of the disclosed technique, and located within a catheter generally referenced 152. Electromagnetic field detector 150 includes an electromagnetic coil 154 and a core 156. Catheter 152 includes a medical operational element 158 located at a distal portion 160 of catheter 152. Catheter 152 includes a longitudinal channel 162 for the passage of a material or an element 164 there through. Core 156 includes a perforation 166 for the passage of material or element 164 there through. Electromagnetic coil 154 is coupled with a position and orientation determining system (not shown) for determining the position and orientation of catheter 152, by electric conductors 168 or by a wireless link.

Electromagnetic field detector 150 is embedded within catheter 152, such that the longitudinal axes of electromagnetic field detector 150 and longitudinal channel 162, are substantially perpendicular. However, the longitudinal axes of perforation 166 and longitudinal channel 162 are substantially parallel or along the same line. Medical operational element 158 is similar to medical operational element 108 (FIG. 1), and hence, perforation 166 allows the passage of material or element 164 there through, such as a guidewire (not shown), or a material or an element associated with the operation of medical operational element 158.

Figure 3:
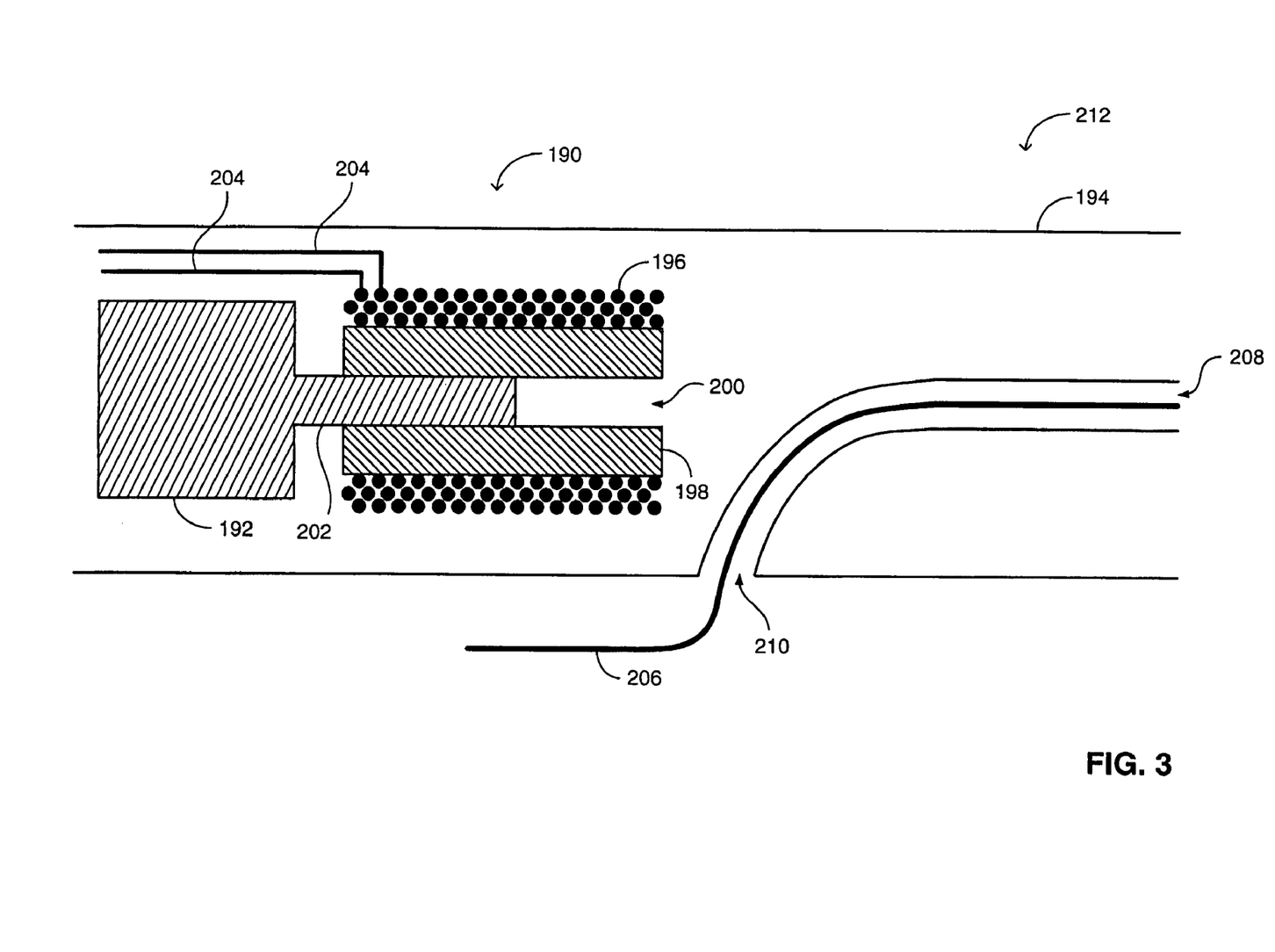
FIG. 3 is a schematic illustration of a cross section of an electromagnetic field detector and a device, constructed and operative in accordance with a further embodiment of the disclosed technique, both the electromagnetic field detector and the device being located within a catheter.

Reference is now made to FIG. 3, which is a schematic illustration of a cross section of an electromagnetic field detector, generally referenced 190, and a device generally referenced 192, constructed and operative in accordance with a further embodiment of the disclosed technique, both the electromagnetic field detector and the device being located within a catheter generally referenced 194. Electromagnetic field detector 190 is similar to electromagnetic field detector 100 (FIG. 1). Device 192 is a device which is normally incorporated with catheter 194, such as an image detector, imaging device (e.g., IVUS, OCT, MRI), and the like. Electromagnetic field detector 190 includes an electromagnetic coil 196 and a core 198. Core 198 includes a perforation 200 (i.e., an adaptive feature) for coupling electromagnetic field detector 190 with device 192. The longitudinal axis of perforation 200 is substantially parallel with the longitudinal axis of catheter 194 or it lies substantially along the same line. Device 192 includes a protrusion 202 (i.e., a mating feature) to fit perforation 200. A biocompatible adhesive can be employed for securing protrusion 202 within perforation 200. Electromagnetic coil 196 is coupled with a position and orientation determining system (not shown) for determining the position and orientation of device 192, by electric conductors 204.

Catheter 194 is a rapid-exchange type catheter, i.e., a guidewire 206 enters a longitudinal channel 208 of catheter 194 through a side opening 210 of catheter 194, substantially close to a distal portion 212 of catheter 194. Electromagnetic field detector 190 and device 192 are located within catheter 194 proximal to side opening 210.

The longitudinal axes of perforation 200 and longitudinal channel 208 are substantially parallel or lie substantially along the same line. The longitudinal axes of perforation 200 and protrusion 202 lie substantially along the same line. Preferably, device 192 can rotate about an axis substantially along or parallel with the longitudinal axis of longitudinal channel 208. Rotation of device 192 provides for easy installation, and may be required for the effective operation of a device such as an IVUS. The coupling between electromagnetic field detector 190 and device 192 via perforation 200 and protrusion 202, allows alignment of the longitudinal axes of perforation 200 and protrusion 202. Hence, the position and orientation determining system can determine the position and orientation of device 192, as well as of catheter 194 in the vicinity of side opening 210. Side opening 210 is adjacent the distal tip of catheter 194, thus the position and orientation of device 192 also indicates the position and orientation of the distal tip of catheter 194.

In the example set forth in FIG. 3, electromagnetic field detector 190 is located between side opening 210 and device 192. It is noted that device 192 can be coupled to electromagnetic field detector 190, such that device 192 is located between side opening 210 and electromagnetic field detector 190.

Figure 4:
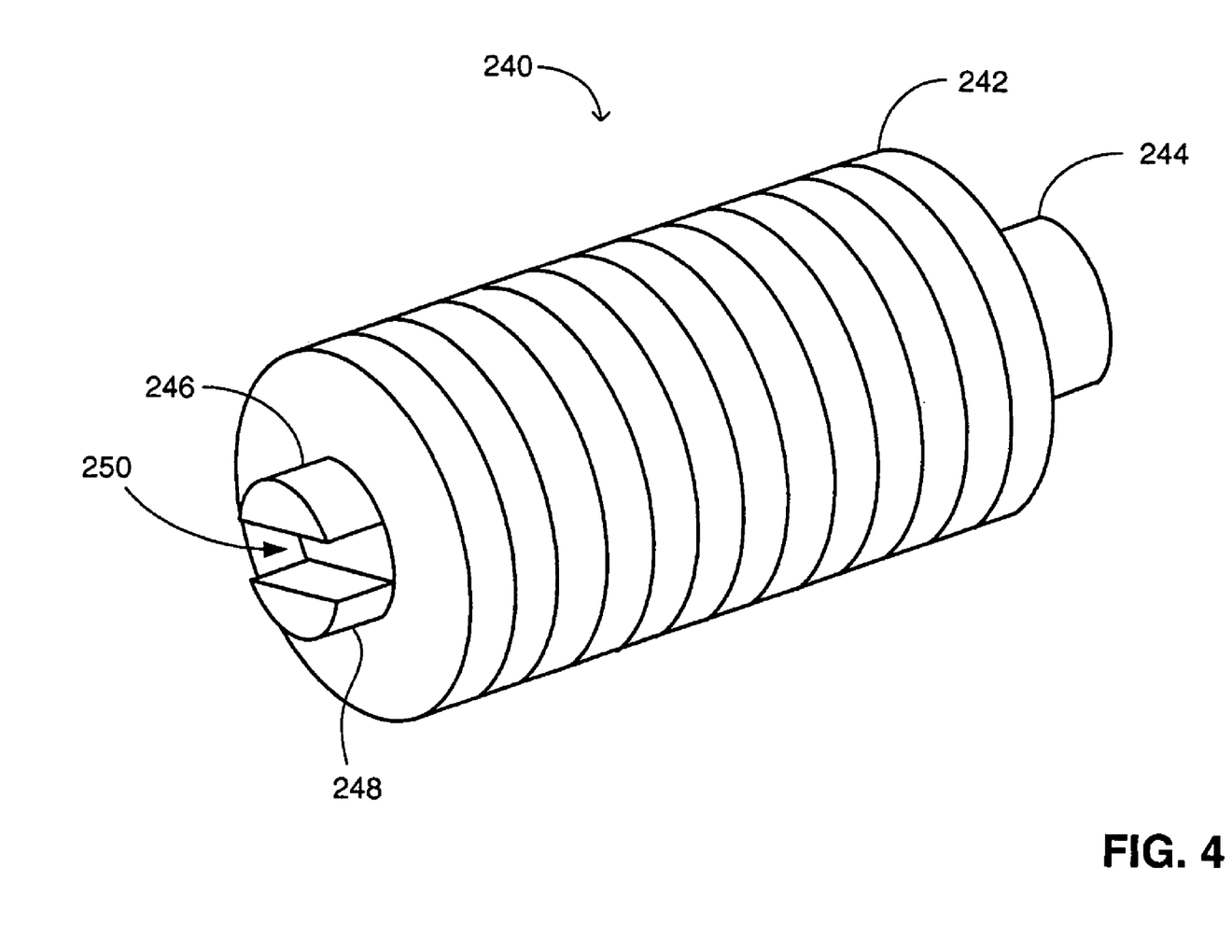
FIG. 4 is a schematic illustration in perspective of an electromagnetic field detector constructed and operative in accordance with another embodiment of the disclosed technique.

Reference is now made to FIG. 4, which is a schematic illustration in perspective of an electromagnetic field detector, generally referenced 240, constructed and operative in accordance with another embodiment of the disclosed technique. Electromagnetic field detector 240 includes an electromagnetic coil 242 wound around a core 244. One end of core 244 includes two protrusions 246 and 248 (i.e., an adaptive feature). Protrusions 246 and 248 are spaced apart opposing segments of core 244. Thus, protrusions 246 and 248 form a notch 250 there between. A mating feature of a device (not shown) equivalent to device 192 of FIG. 3 (e.g., a protrusion whose cross section is compatible with notch 250), makes possible to couple electromagnetic field detector 240 with the device. The core beyond notch 250 can be hollow similar to the perforated cores of FIGS. 1 to 3, or solid similar to core 278 of FIG. 5, as decribed herein below.

Figure 5:
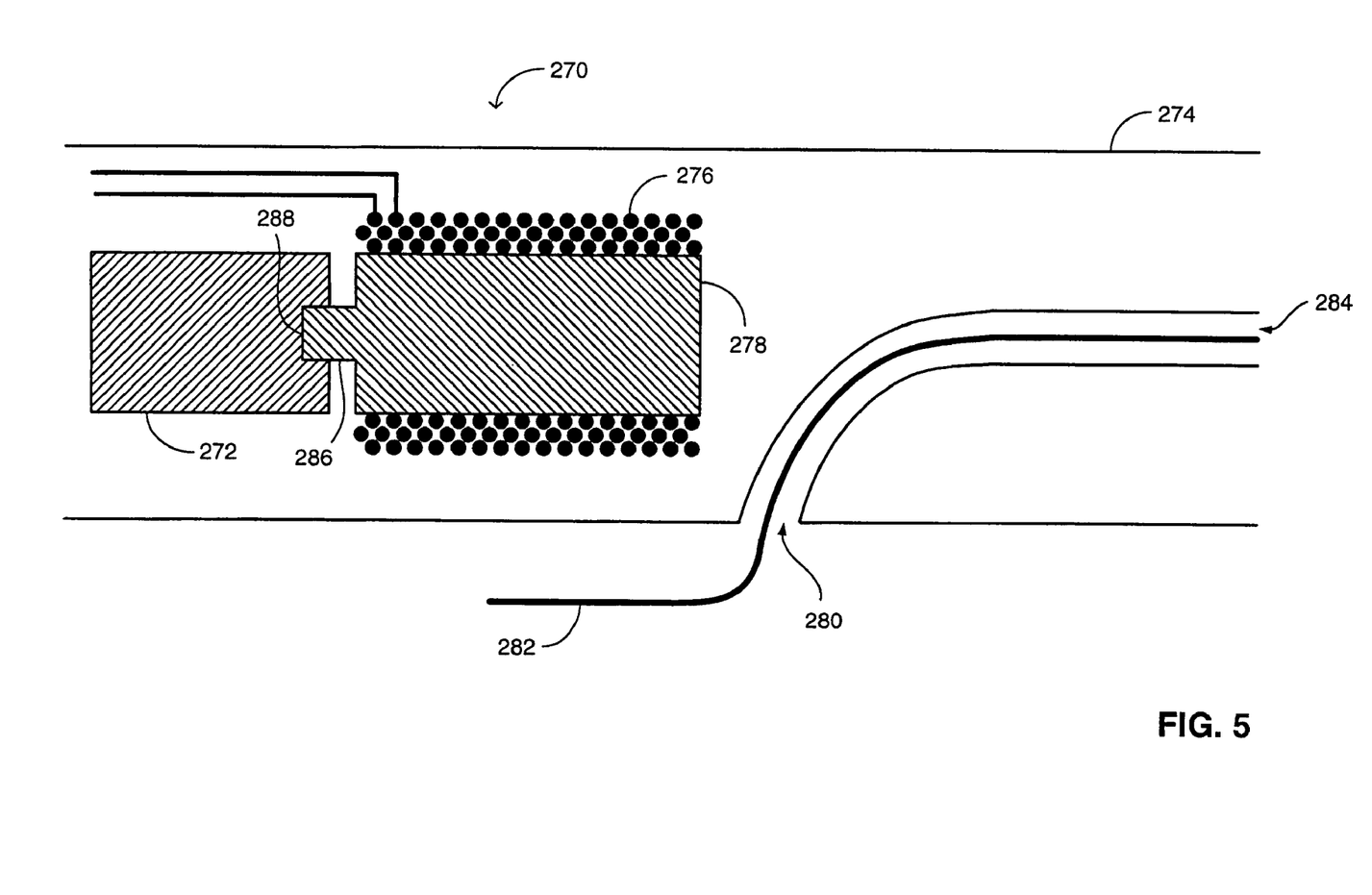
FIG. 5 is a schematic illustration of a cross section of an electromagnetic field detector and a device, constructed and operative in accordance with a further embodiment of the disclosed technique, both the electromagnetic field detector and the device being located within a catheter.

Reference is now made to FIG. 5, which is a schematic illustration of a cross section of an electromagnetic field detector, generally referenced 270, and a device generally referenced 272, constructed and operative in accordance with a further embodiment of the disclosed technique, both the electromagnetic field detector and the device being located within a catheter generally referenced 274. Electromagnetic field detector 270 includes an electromagnetic coil 276 and a core 278. Catheter 274 is a rapid-exchange type catheter similar to catheter 194 (FIG. 3), having a side opening 280 for entering a guidewire 282 into a longitudinal channel 284 of catheter 274. Device 272 is similar to device 192 (FIG. 3).

Core 278 includes a protrusion 286 (i.e., an adaptive feature) on one side thereof. The cross section of protrusion 286 can be circular as well as polygonal, such as a rectangle, square, and the like. The longitudinal axis of protrusion 286 lies substantially along the longitudinal axis of core 278. Device 272 includes a cavity 288 (i.e., a mating feature) of a size and a shape to fit protrusion 286. The longitudinal axis of cavity 288 lies substantially along the longitudinal axis of device 272. Device 272 is coupled with electromagnetic field detector 270, by assembling protrusion 286 on to cavity 288. A biocompatible adhesive can be employed in assembling protrusion 286 on to cavity 288.

In the example set forth in FIG. 5, electromagnetic field detector 270 is located between side opening 280 and device 272. It is noted that device 272 can be coupled to electromagnetic field detector 270, such that device 272 is located between side opening 280 and electromagnetic field detector 270.

Figure 6:
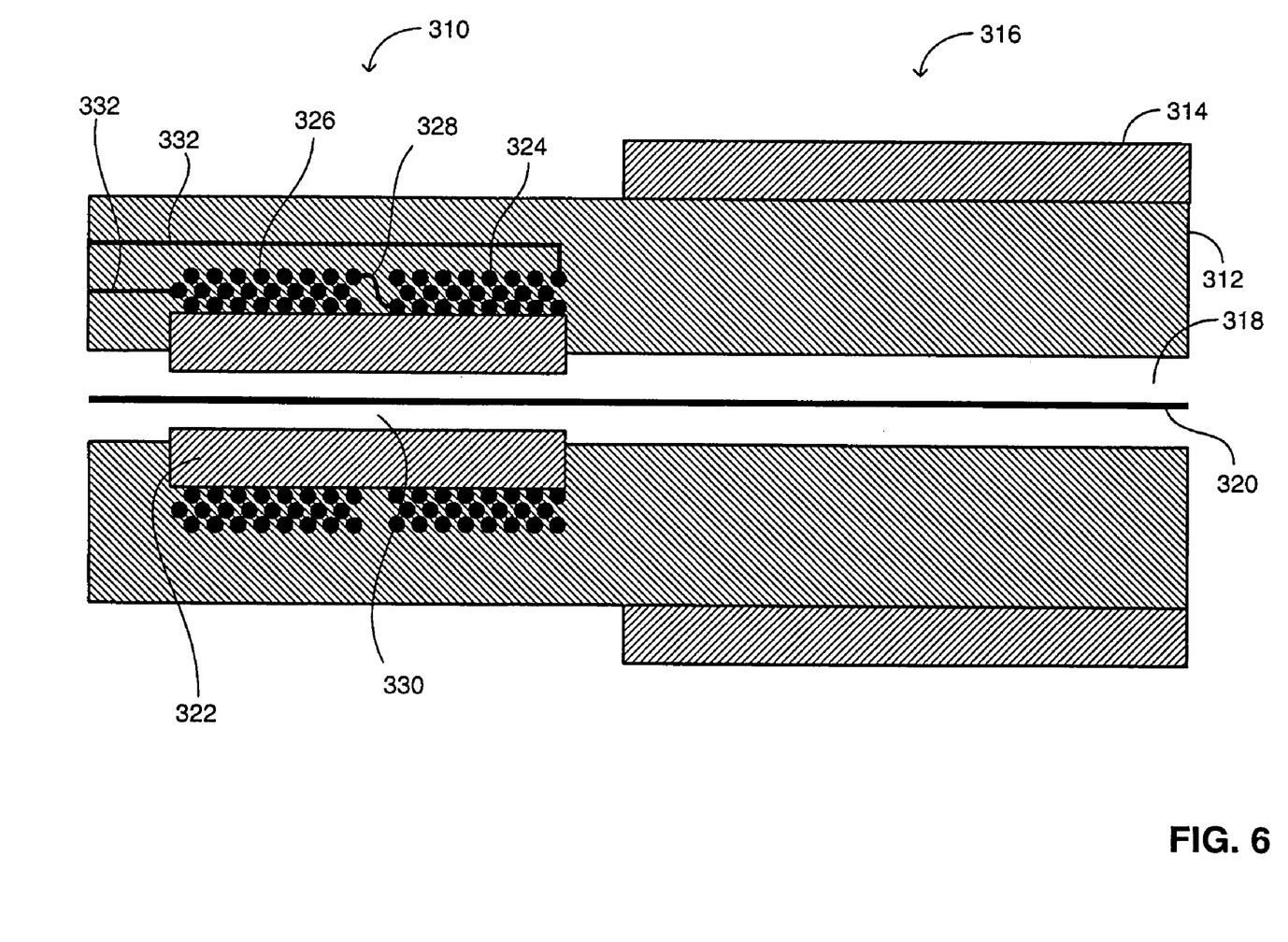
FIG. 6 is a schematic illustration of a cross section of an electromagnetic field detector constructed and operative in accordance with a further embodiment of the disclosed technique, and located within a catheter.

Reference is now made to FIG. 6, which is a schematic illustration of a cross section of an electromagnetic field detector, generally referenced 310, constructed and operative in accordance with a further embodiment of the disclosed technique, and located within a catheter generally referenced 312. Catheter 312 includes a medical operational element 314 either at a distal portion 316 thereof or a mid-portion (not shown) thereof. Catheter 312 includes a longitudinal channel 318 for example for passage of a material or an element 320 there through (e.g., a guidewire).

Electromagnetic field detector 310 includes a core 322 and one or more electromagnetic coils 324 and 326. Electromagnetic coils 324 and 326 are wound around core 322 and are connected together by an electric conductor 328. Core 322 includes a perforation 330 to allow passage of element 320. Electromagnetic coils 324 and 326 are coupled to a position and orientation determining system (not shown) by electric conductors 332, for determining the position and orientation of catheter 312 or selected portions thereof, such as distal portion 316, or medical operational element 314. Since electromagnetic field detector 310 includes more electromagnetic coils than electromagnetic field detector 100 (FIG. 1), the capacitance of electromagnetic field detector 310 is less than that of electromagnetic field detector 100.

It will be appreciated by persons skilled in the art that the disclosed technique is not limited to what has been particularly shown and described hereinabove. Rather the scope of the disclosed technique is defined only by the claims, which follow.

The invention claimed is:

1. Electromagnetic field detector located within a catheter, for determining the position and orientation of the catheter according to an electromagnetic field generated in the vicinity of the catheter, the catheter including a distal tip and the distal tip including a proximal side and a distal side, the electromagnetic field detector comprising:
   a ferromagnetic core having a perforation, said perforation providing communication between a first side of said ferromagnetic core and a second side of said ferromagnetic core, said first side facing said proximal side and said second side facing said distal side; and at least one winding wound around said ferromagnetic core, said at least one winding being coupled with a position and orientation determining system, said at least one winding producing a current according to said electromagnetic field, said position and orientation determining system determining said position and orientation according to said current, wherein said ferromagnetic core increases the sensitivity of said electromagnetic field detector to said electromagnetic field, by increasing a proportionality factor between said current and said electromagnetic field.

2. The electromagnetic field detector according to claim 1, wherein said perforation provides conveyance of a material through said perforation.

3. The electromagnetic field detector according to claim 2, wherein said material is selected from the group consisting of:
pharmaceutical substance; and
cryogenic fluid.

4. The electromagnetic field detector according to claim 1, wherein said perforation provides conveyance of an element through said perforation.

5. The electromagnetic field detector according to claim 4, wherein said element is selected from the group consisting of:
guidewire;
substance delivery lumen;
electric conductor;
optical conductor;
flexible shaft; and
medical element.

6. The electromagnetic field detector according to claim 1, wherein an inner wall of said perforation includes a biocompatible coating.

7. The electromagnetic field detector according to claim 6, wherein said biocompatible coating is selected from the group consisting of:
Parylene;
polyimide;
Teflon; and
drug.

8. The electromagnetic field detector according to claim 6, wherein said biocompatible coating has a property selected from the group consisting of:
hydrophilic; and
hydrophobic.

9. The electromagnetic field detector according to claim 1, wherein an electric shield encompasses said at least one winding.

10. The electromagnetic field detector according to claim 9, wherein said electric shield is in the form of a foil comprising an electrically conductive material.

11. The electromagnetic field detector according to claim 9, wherein said electric shield is in the form of a complete cylinder.

12. The electromagnetic field detector according to claim 9, wherein said electric shield is in the form of a partial cylinder.

13. The electromagnetic field detector according to claim 9, wherein said electric shield is in the form of an electrically conductive coating.

14. The electromagnetic field detector according to claim 1, wherein said at least one winding is coupled together by at least one electrical conductor.

15. Electromagnetic field detector located within a catheter, for determining the position and orientation of the catheter according to an electromagnetic field generated in the vicinity of the catheter, the catheter being incorporated with a medical operational device for performing a diagnostic or therapeutic medical operation, the electromagnetic field detector comprising:

a ferromagnetic core having at least one adaptive feature for connecting said ferromagnetic core to said medical operational device;

a mating feature to be connected to said adaptive feature, said mating feature being incorporated with said medical operational device; and at least one winding wound around said ferromagnetic core, said at least one winding being coupled with a position and orientation determining system, said at least one winding producing a current according to said electromagnetic field, said position and orientation determining system determining said position and orientation according to said current, wherein said ferromagnetic core increases the sensitivity of said electromagnetic field detector to said electromagnetic field, by increasing a proportionality factor between said current and said electromagnetic field.

16. The electromagnetic field detector according to claim 15, wherein said at least one adaptive feature is in the form of at least one protrusion protruding from said ferromagnetic core, and wherein said mating feature is in the form of at least one cavity, in a size and a shape to fit a respective one of said at least one protrusion.

17. The electromagnetic field detector according to claim 16, wherein said at least one protrusion comprises two protrusions in the form of two spaced apart opposing segments of a circle, thereby forming a notch between said two protrusions, and wherein said mating feature is in the form of a device protrusion, in a size and a shape to fit said notch.

18. The electromagnetic field detector according to claim 15, wherein said at least one adaptive feature is in the form of a perforation, and wherein said mating feature is in the form of a device protrusion, in a size and a shape to fit at least a portion of said perforation.

19. The electromagnetic field detector according to claim 15, wherein said medical operational device is selected from the group consisting of:
image detector;
intravascular ultrasound device;
coherence tomography device;
magnetic resonance imaging device;
valve;
suturinig device;
implant;
biological marker;
radiopaque marker;
substance delivery device;
diagnostic device;
miniature camera;
infrared camera;
pressure sensor;
temperature sensor;
pH sensor;
valvuloplasty operation device;
expansion unit;
baloon;
stent;

balloon expanding stent;
ablation unit;
laser;
cryogenic fluid unit;
electric impulse unit;
cutting balloon;
rotational atherectomy unit;
rotablator;
directional atherectomy unit;
transluminal extraction unit;
substance delivery unit;
coated stent;
drug delivery balloon; and
brachytherapy unit.

20. Position and orientation determining system, for determining the position and orientation of a catheter, the catheter including a distal tip and the distal tip including a proximal side and a distal side, the position and orientation determining system comprising:

an electromagnetic field generator for generating an electromagnetic field in the vicinity of said catheter; and an electromagnetic field detector located within said catheter, said electromagnetic field detector comprising:

a ferromagnetic core having a perforation, said perforation providing a communication between a first side of said ferromagnetic core and a second side of said ferromagnetic core, said first side facing said proximal side and said second side facing said distal side; and at least one winding wound around said ferromagnetic core, said at least one winding producing a current according to said electromagnetic field, said position and orientation determining system determining said position and orientation according to said current, wherein said ferromagnetic core increases the sensitivity of said electromagnetic field detector to said electromagnetic field, by increasing a proportionality factor between said current and said electromagnetic field.

* * * * *